(12) United States Patent
Gallastegui et al.

(10) Patent No.: US 9,950,931 B2
(45) Date of Patent: Apr. 24, 2018

(54) CROSS-LINKED GRAPHENE NETWORKS

(71) Applicants: THE BIO NANO CENTRE LIMITED, London (GB); KING ABDULAZIZ UNIVERSITY, Jeddah (SA)

(72) Inventors: Ainara Garcia Gallastegui, London (GB); Milo Shaffer, London (GB); Abdulrahman O. Alyoubi, Jeddah (SA); Abdullah M Asiri, Jeddah (SA)

(73) Assignees: THE BIO NANO CENTRE LIMITED, London (GB); KING ABDULAZIZ UNIVERSITY, Jeddah (SA)

(*) Notice: Subject to any disclaimer, the term of this patent is extended or adjusted under 35 U.S.C. 154(b) by 747 days.

(21) Appl. No.: 14/383,800

(22) PCT Filed: Mar. 7, 2013

(86) PCT No.: PCT/GB2013/050571
§ 371 (c)(1),
(2) Date: Sep. 8, 2014

(87) PCT Pub. No.: WO2013/132260
PCT Pub. Date: Sep. 12, 2013

(65) Prior Publication Data
US 2015/0122800 A1    May 7, 2015

(30) Foreign Application Priority Data
Mar. 9, 2012  (GB) ................................. 1204170.3

(51) Int. Cl.
| | | |
|---|---|---|
| C01B 31/04 | (2006.01) | |
| B82Y 30/00 | (2011.01) | |
| B82Y 40/00 | (2011.01) | |
| C07D 303/40 | (2006.01) | |
| H05B 3/00 | (2006.01) | |
| H05B 3/14 | (2006.01) | |
| C01B 32/23 | (2017.01) | |
| C01B 32/182 | (2017.01) | |
| C01B 32/194 | (2017.01) | |

(52) U.S. Cl.
CPC .......... *C01B 31/0484* (2013.01); *B82Y 30/00* (2013.01); *B82Y 40/00* (2013.01); *C01B 32/182* (2017.08); *C01B 32/194* (2017.08); *C01B 32/23* (2017.08); *C07D 303/40* (2013.01); *H05B 3/0004* (2013.01); *H05B 3/145* (2013.01); *B01J 2231/005* (2013.01)

(58) Field of Classification Search
CPC .............. C01B 31/0484; C01B 31/043; C01B 31/0438; H05B 3/145; H05B 3/0004; C07D 303/40; B82Y 40/00; B82Y 30/00; B01J 2231/005
See application file for complete search history.

(56) References Cited

U.S. PATENT DOCUMENTS

2011/0224376 A1  9/2011 Zhai et al.
2012/0034442 A1  2/2012 Pauzauskie

FOREIGN PATENT DOCUMENTS

WO    WO 2009/085015    7/2009

OTHER PUBLICATIONS

Cai et al., "Synthesis and solid-state NMR structural characterization of 13C-labeled graphite oxide," *Science*, 321(5897):1815, 2008.
Chen and Yan, "In situ self-assembly of mild chemical reduction graphene for three-dimensional architectures," *Nanoscale*, 3:3132-3137, 2011.
Chen et al., "Preparation of graphene by the rapid and mild thermal reduction of graphene oxide induced by microwaves," *Carbon*, 48(4):1146-1152, 2010.
Gao et al., "New insights into the structure and reduction of graphite oxide," *Nat. Chem.*, 1(5):403-8, 2009.
Geim et al., "Graphene: status and prospects," *Science*, 324(5934):1530-1534, 2009.
Hummers and Offema, "Preparation of Graphitic Oxide," *J. Am. Chem. Soc.*, 80(6):1339, 1958.
Jiang et al., "Self-assembly of reduce graphene oxide into three-dimensional architecture by divalent ion linkage," *J. Phys. Chem.*, 114:22462-22465, 2010.
Liu and Seo, "A Controllable Self-Assembly Method for Large-Scale Synthesis of Graphene Sponges and Free-Standing Graphene Films," *Adv. Funct. Mater.*, 20:1930-1936, 2010.
Liu et al., "Gelation in carbon nanotube/polymer composites," *Polymer*, 44(24):7529-7532, 2003.
Niyogi et al., "Solution properties of graphite and graphene," *J. Am. Chem. Soc.*, 128:7720, 2006.
Novoselov et al., "Electric field effect in atomically thin carbon films," *Science*, 306(5696):666-669, 2004.
PCT International Search Report and Written Opinion issued in International Patent Application No. PCT/GB2013/050571, dated Feb. 17, 2014.
Tang et al., "Noble-metal-promoted three-dimensional macroassembly of single-layered graphene oxide," *Angew. Chem. Int. Ed.*, 49:4603-4067, 2010.
Veca et al., "Polymer functionalization and solubilization of carbon nanosheets," *Chem. Commun. (Camb.)*, 18:2565-2567, 2009.
Worsley et al., "High surface area, sp2-cross-linked three-dimensional graphene monoliths," *Journal of Physical Chemistry Letters*, 2(8):921-925, 2011.
Worsley et al., "Synthesis of graphene aerogel with high electrical conductivity," *J. Am. Sci. Soc.*, 132(40):14067-14069, 2010.

(Continued)

*Primary Examiner* — Richard M Rump
(74) *Attorney, Agent, or Firm* — Parker Highlander PLLC

(57) ABSTRACT

The present invention relates to a method for the production of cross-linked graphene and graphene oxide networks, which are selected from aerogels and xerogels with improved performance and characteristics thereof. The invention is also concerned with graphene and graphene oxide networks, which are selected from aerogels and xerogels produced by such processes and uses thereof.

13 Claims, No Drawings

(56) References Cited

OTHER PUBLICATIONS

Xu et al., "Self-assembled graphene hydrogel via a one-step hydrothermal process," *ACS Nano*, 4(7):4324-4330, 2010.
Yan et al., "Chemistry and physics of a single atomic layer: strategies and challenges for functionalization of graphene and graphene-based materials," *Chem. Soc. Rev.*, 41(1):97-114, 2012.
Zhang et al., "Mechanically strong and highly conductive graphene aerogel and its use as electrodes for electrochemical power sources," *Journal of Materials Chemistry*, 21(18):6494-6497, 2011.

CROSS-LINKED GRAPHENE NETWORKS

This application is a national phase application under 35 U.S.C. § 371 of International Application No. PCT/GB2013/050571, filed Mar. 7, 2013, which claims the benefit of priority to United Kingdom Patent Application No. 1204170.3, filed Mar. 9, 2012. The entire contents of the above-referenced disclosures are specifically incorporated herein by reference.

FIELD OF THE INVENTION

The present invention relates to a method for the production of cross-linked graphene and graphene oxide networks, which are selected from aerogels and xerogels with improved performance and characteristics thereof. The invention is also concerned with graphene and graphene oxide networks, which are selected from aerogels and xerogels produced by such processes and uses thereof.

BACKGROUND OF THE INVENTION

Xerogels and aerogels are highly porous materials with a particularly low envelope density and high surface area. They typically also display exceptionally low thermal conductivity and acoustic propagation properties. As such, they are useful in a wide range of applications including as purification/separation media, non-reflective panels, gas storage media, catalyst support, porous substrates e.g. sponges and electrochemical device electrodes (for supercapacitors, fuel cells and lithium ion batteries).

The most common examples are silica aerogels usually made by sol-gel processes and carbon hydrogels obtained from pyrolysis of resorcinol-formaldehyde resin.

Graphene is a single sheet of carbon atoms patterned in a honeycomb lattice form. Graphene has recently attracted much attention for its unique electronic properties, excellent mechanical properties, and superior thermal properties (K. S. Novoselov, A. K. Geim, S. V. Morozov, D. Jiang, Y. Zhang, S. V. Dubonos, I. V. Grigorieva and A. A. Firsov, Science, 2004, 306, 666-669 and A. K. Geim, Science, 2009, 324, 1530-1534). Attempts to exploit these properties in macroscopic form depend on the development of appropriate processing techniques.

Graphene aerogel with high electrical conductivity ($1\times10^2$ S m$^{-1}$) has been synthesised by sol-gel polymerization of resorcinol (R) and formaldehyde (F) with sodium carbonate as a catalyst (C) in an aqueous suspension of graphene oxide (GO) (M. A. Worsley, P. J. Pauzauskie, T. Y. Olson, J. Biener, J. H. Satcher, T. F. Baumann, J. Am. Chem. Soc., 2010, 132, 14067-14069)

Ion linkages have also been applied for the preparation of 3D architectures of graphene (Z. H. Tang, S. L. Shen, J. Zhuang and X. Wang, Angew. Chem., Int. Ed., 2010, 49, 4603-4607; X. Jiang, Y. Ma, J. Li, Q. Fan and W. Huang, J. Phys. Chem. C, 2010, 114, 22462).

Graphene oxide sponges were synthesised by vacuum centrifugal evaporating system (F. Liu, T. S. Seo, Adv. Funct. Mater., 2010, 20, 1930-1936).

Graphene hydrogel has been prepared by an hydrothermal process under high pressure, and the obtained hydrogel is electrically conductive, mechanically strong, and exhibits a high specific capacitance (Y. X. Xu, K. X. Sheng, C. Li, G. Q. Shi, ACS Nano, 2010, 4, 4324-4330).

3D architectures of graphene have been fabricated via an in situ self-assembly of graphene obtained by mild chemical reduction of graphene oxide in water under atmospheric pressure (W. Chen, L. Yan, 2011, Nanoscale, 3, 3132-3137).

Therefore, the present invention seeks to provide a method of obtaining cross-linked graphene and graphene oxide networks, which are selected from aerogels and xerogels. The present invention also seeks to provide cross-linked graphene networks which are selected from aerogels and xerogels which allow more control over the density, shape, conductivity and internal surface of the graphene, so that they display desirable electrical and mechanical properties.

The present invention also seeks to utilise such electrically heatable graphene and graphene oxide aerogels/xerogels which have high surface area, and are highly interconnected to provide robust networks that are attractive for applications such as filtration, sorption, gas storage and catalyst support.

SUMMARY OF THE INVENTION

According to a first aspect of the present invention, there is provided a method of producing an aerogel or xerogel comprising graphene, graphene oxide or a mixture thereof, comprising the steps of:
  a) dispersing graphene, graphene oxide or a mixture thereof in a solvent compatible therewith;
  b) cross-linking said graphene, graphene oxide or a mixture thereof via functional groups present on the graphene and/or the graphene oxide, or with a linking molecule comprising at least two functional sites capable of reacting with the surface of said graphene and/or graphene oxide, to form a covalently cross-linked gel network; and
  c) removing said solvent to produce a cross-linked aerogel or xerogel with a solvent content of less than 10%.

Preferably, in the above method, direct condensation of graphene oxide takes place, without the presence of linker molecules, i.e., additional linker molecules other than those present as oxides on the surface of the graphene oxide. This type of direct condensation of graphene oxide allows close approach and low interflake resistance of the graphene oxide sheets. It also provides for a simple process and work up, with no excess reagents being required.

Preferably, in the above method, where a linking molecule is used to cross-link, it is preferably used with pristine graphene. This type of direct reaction preserves graphene properties better than graphene oxide. It avoids a graphene oxidation step which can be aggressive and wasteful.

Preferably, in the above method, where a linking molecule is used to cross-link, it is preferably not used with graphene oxide.

Preferably, the solvent content of the cross-linked aerogel or xerogel according to the invention is less than 2% by weight, more preferably less than 0.5% by weight, more preferably less than 0.1% by weight.

Graphene or graphene oxide used in the present invention is reacted using functional groups already present on the graphene oxide, or with a linking molecule comprising at least two functional sites capable of reacting with the surface of said graphene or graphene oxide, to form a covalently cross-linked gel network.

As used herein, "graphene aerogel" or "graphene oxide aerogel" means an aerogel comprising—graphene or graphene oxide respectively. Further materials may be present in the aerogel. Alternatively, no further materials are present other than residual reagent materials, gas and/or solvents.

As used herein, "graphene xerogel" or "graphene oxide xerogel" means a xerogel comprising graphene or graphene oxide respectively. Further materials may be present in the xerogel. Alternatively, no further materials are present other than residual reagent materials, gas and/or solvents.

Unless further specified herein, reference herein to an "aerogel" is deemed to refer to an aerogel comprising graphene or graphene oxide.

Unless further specified herein, reference herein to a "xerogel" is deemed to refer to a xerogel comprising graphene or graphene oxide.

In terms of chemical reactions, acylation reactions are among the most common approaches used for linking molecular moieties onto oxygenated groups at the edges of graphene oxide. The acylation reaction between the carboxyl acid groups of graphene oxide and octadecylamine (after $SOCl_2$ activation of the COOH groups) can be used to modify graphene oxide by long alkyl chains (S. Niyogi, E. Bekyarova, M. E. Itkis, J. L. McWilliams, M. A. Hamon and R. C. Haddon, J. Am. Chem. Soc., 2006, 128, 7720).

Besides small organic molecules, graphene nanosheets can be functionalized with polymers like poly(vinyl alcohol) (PVA) through the carbodiimide-activated esterification reaction between the carboxylic acid moieties on the nanosheets and hydroxyl groups on PVA using N,N-dicyclohexylcarbodiimide (DCC), 4-(dimethylamino)-pyridine (DMAP), and N-hydroxybenzotriazole (HOBT) in DMSO (L. M. Veca, F. Lu, M. J. Meziani, L. Cao, P. Zhang, G. Qi, L. Qu, M. Shrestha and Y. P. Sun, Chem. Commun., 2009, 2565).

According to one embodiment of the present invention, the linking molecule may have functionalities that can couple directly to the graphene or graphene oxide surface. For example, bis(diazonium) salts, or multifunctional molecules suitable for 1,3-dipolar cycloadditions, or Bingel condensations using known graphene or graphene oxide surface chemistry.

More generally, radical addition, electrophile addition or cycloaddition, or all the reactions involving the reduction of the graphenes followed by the reaction of the graphene with an electrophilic cross-linking molecule is of interest. Such reductions may be carried out by the addition of electrons (reduction) to the graphene layers. One example uses ternary potassium salt $K(THF)xC_{24}$ (THF) tetrahydrofurane, where x=1-3.

Direct coupling to the sidewalls, avoids the necessity for damaging pre-oxidation steps. By avoiding unstable linking groups, a more thermally and chemically stable framework can be produced, of greater versatility in application, for example, by creating an aerogel linked by only carbon-carbon bonds. Direct coupling is particularly amenable to creating conjugated linking systems that aid electrical conductivity. In addition, some direct chemistries, such as alkylation following the reductive charging in Birch reactions, are particularly helpful for improving the dispersion of the graphenes to form a good gel and hence a homogeneous aerogel.

Alternatively, according to a preferred embodiment, such a linking molecule may react with oxide groups of graphene oxide to produce, for example, ester, ether, or amide linkages. Suitable cross-linking agents, include alkyl diamines, aromatic diamines, alkyl diols, aromatic diols, polyols, bis-sodium alkoxides, dicarboxylic acids, di acid chlorides, di siloxane halides, di siloxane alkoxides, preferably $C_{1-20}$ alkyl diamines, $C_{5-24}$ aromatic diamines, $C_{1-20}$ alkyl diols, $C_{5-20}$ aromatic diols, $C_{2-100}$ polyols, bis-sodium $C_{1-20}$ alkoxides, $C_{2-20}$ dicarboxylic acids, $C_{2-20}$ di acid chlorides, more preferably $C_{1-10}$ alkyl diamines, $C_{6-18}$ aromatic diamines, $C_{2-10}$ alkyl diols, $C_{6-18}$ aromatic diols, $C_{2-20}$ polyols, bis-sodium $C_{2-10}$ alkoxides, $C_{2-10}$ dicarboxylic acids, $C_{2-10}$ di acid chlorides, and the like. Preferably, the two reactive groups are located on different atoms of the linking molecule, more preferably at some distance, to maximise the chance of reacting with two different graphene molecules. The use of small rigid molecules may maximise the chance of establishing a cross-link, for example using 1,4-diamino benzene, by limiting the possibility of reacting twice with the same graphene molecule.

In an alternative, preferred embodiment, the graphene oxide used in the present invention are cross-linked using any linking groups which are capable of forming covalent bonds by direct reaction between the oxides on the graphene surface. In this case, there is no additional linking molecule interposed between the graphene oxide; the covalent bond forms directly by condensation between the existing oxide groups. This approach has the advantage of bringing the graphenes into close contact, maximising the electrical conductivity of the junction, and minimising both the additional reagents required and subsequent parasitic mass added to the network. It is worth noting that, in the previous embodiment, the additional linking molecules will saturate the entire surface, although graphene cross-links will only occur relatively rarely. These molecules may be wasteful and may, undesirably, occlude the conductive surface that is desirable in certain applications such as electrochemical electrodes. Direct condensation between the existing surface oxides occurs only at the contact points between the graphenes, leaving the remaining surface unchanged, or available for subsequent differential functionalisation.

As disclosed previously, the preferred embodiments according to the present invention may involve the use of graphene oxide which may be obtained commercially or, more usually, be those that have further been oxidised according to any standard method.

The term "graphene oxide" as used herein refers to any graphene with one or more oxide groups present on the surface of the graphene. A wide range of surface oxides are known in carbon chemistry. In the present invention, the "oxide groups" are selected from the group consisting of quinones, ketones, lactones, pyrones, carboxylic acids, carboxylates, hydroxides and hydroxyl groups, and groups derivable from these via oxidation, and mixtures of two or more thereof. In a particularly preferred embodiment, the surface oxides are carboxylic and/or hydroxide groups.

The level of oxidation of the graphenes will vary according to the desired mechanical and electrical properties required. Typically, the level of oxidation on the oxidised graphenes is between 0.001-100 mmol/g, preferably 0.1 mmol/g or greater.

Three experimental chemical routes have been developed for graphene oxidation. The first is a one-step process, and is achieved through direct oxidisation of graphene with strong oxidants such as concentrated sulfuric acid, concentrated nitric acid, or potassium permanganate. The second is a two-step process, in which graphite is oxidized through Hummers', Brodies', Staudenmaiers', or modified Hummer's methods, or (W. Hummers and R. Offema, J. Am. Chem. Soc., 1958, 80, 1339; W. F. Chen, L. F. Yan and P. R. Bangal, Carbon, 2010, 48, 1146-1152) electrochemical oxidation, followed by exfoliating or thermally expanding the graphene oxide obtained. The third is a physicochemical process: graphene oxide nanoribbons are created through lengthwise cutting and unravelling the sidewalls of multi-walled carbon nanotube (MWCNTs) by oxidative processes (L. Yan, Y. B. Zheng, F. Zhao, S. Li, X. Gao, B. Xu, P. S. Weiss, Y. Zhao, Chem. Soc. Rev., 2012, 41, 97-114).

The acid oxidation of graphite generates oxygenated species like carboxyl, epoxy and hydroxyl on the material, generating graphene oxide (W. Gao, L. B. Alemany, L. J. Ci and P. M. Ajayan, Nat. Chem., 2009, 1, 403; W. Cai, R. D. Piner, F. J. Stadermann, S. Park, M. A. Shaibat, Y. Ishii, D. Yang, A. Velamakanni, S. J. An and M. Stoller, Science, 2008, 321, 1815).

In a preferred method, the graphene oxide is cross-linked to form an ester or ether bond, most preferably an ester bond. The reaction is preferably a condensation reaction, one that releases a small molecule by product such as water, rather than introducing additional atoms into the resulting linkage. In yet another embodiment, the surface oxides may be converted to other simple functional groups for direct condensation. In such an embodiment, the surface alcohols on the graphenes may be converted to, for example, an amine functionality, which subsequently allows the cross-links to be formed via an amide bond. Other direct molecular condensations such as those to form imines, thioethers, thioesters, and ureas, also fall within the scope of the present invention.

In a preferred embodiment, the cross-links between the graphene oxides may be formed using a coupling agent. The term "coupling agent" as used herein does not have the conventional meaning often used in polymer resin chemistry but refers to any substance capable of facilitating the formation of a bonding link between two reagents, as in the field of organic chemistry. Such compounds include N,N'-dicyclohexylcarbodiimide (DCC), N,N'-diisopropylcarbodiimide (DIC), ethyl-(N',N'-dimethylamino)propylcarbodiimide hydrochloride (EDC) [adding an equivalent of 1-hydroxybenzotriazole (HOBt) to minimize the racemisation], 4-(N,N-dimethylamino) pyridine (DMAP), (benzotriazol-1-yloxy)tris(dimethylamino)phosphonium hexafluorophosphate (BOP), (benzotriazol-1-yloxy)tripyrrolidinophosphonium hexafluorophosphate, bromotripyrrolidinophosphonium hexafluorophosphate, O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(6-chlorobenzotriazol-1-yl)-N,N,N',N'-tetramethyluronium hexafluorophosphate (HCTU), O-(3,4-dihydro-4-oxo-1,2,3-benzotriazine-3-yl)-N,N,N',N' tetramethyluronium tetrafluoroborate (TDBTU), 3-(diethylphosphoryloxy)-1,2,3 benzotriazin-4(3H)-one (DEPBT), carbonyldilmidazole (CDI) and mixtures thereof.

In a preferred embodiment, a carbodiimide is used to couple a suitable functional group and a carbonyl group such as an ester or an acid. Preferred examples of carbodiimides include but are not limited to 1-ethyl-3-(3-dimethylaminopropyl)carbodiimide, N,N'-dicyclohexyl carbodiimide, N,N'-diisopropyl carbodiimide, bis(trimethylsilyl)carbodiimide and N-cyclohexyl-N'-(β-[N-methylmorpholino]ethyl) carbodiimide p-toluenesulfonate. In a particularly preferred embodiment, the coupling agent is selected from the group consisting of N,N'-dicyclohexylcarbodiimide, N,N'-diisopropylcarbodiimide and 1-ethyl-3-(3-dimethylaminopropyl) carbodiimide.

The coupling agent may be supplemented by an additional agent such as those known to enhance extra selectivity or yield of such condensation reactions, such as N-hydroxybenzotriazole or N-hydroxysuccinimide.

The cross-linking process may be carried out at any reasonable temperature and left for any length of time necessary to complete the reaction, so long as the reaction is carried out at a temperature below the boiling point of the reaction solvent(s). In a preferred method, the reaction is carried out at a temperature of between 15 to 60° C., preferably 20 to 30° C. The reaction time is preferably between 0.1 to 50 hours and more preferably between 1 and 12 hours.

Alternatively, the cross-linking process may be carried out by dehydration. The term dehydration as used herein refers to a chemical reaction which involves the loss of water from the reacting molecule(s). In a preferred embodiment, dehydration is carried out by using groups on the graphene oxide. Such groups include ether linkages which maybe formed by dehydration at a temperature greater than 120° C., preferably greater than 130° C. and even more preferably greater than 150° C., using an acid catalyst. Cross-linking process will require a solvent with a high boiling point, greater than the reaction temperature. In a preferred embodiment, the boiling point of the solvent is greater than 120° C., preferably greater than 130° C. and even more preferably greater than 150° C.

During the course of the reaction, the graphene or graphene oxide is cross-linked to form a gel phase. As used herein, the term "gel" refers to what those skilled in the art understand by the term, and preferably refers to a composition which retains its shape during the drying process. The gel phase is formed by a continuous network of covalently bound graphene or graphene oxide within the solvent. Under small shear deformations the response is predominantly elastic rather than viscous; in dynamic shear rheology experiments, at the gel point there is a characteristic crossover of G' and G"/tan(nπ/2) given by the equation below:

$$G'(\omega)=G''(\omega)/\tan(n\pi/2)=S_g\omega^n\Gamma(1-n)\cos(n\pi/2)$$

where G' is the storage modulus, G" is the loss modulus, Γ is the gamma function, n is the relaxation exponent, $S_g$ is the gel strength and w is the frequency. Using the values of G' at crossover points and the equation described before the $S_g$ value can be estimated, characteristic of the synthesised gel (Gelation in Graphene/Polymer Composites, Liu C. et al., Polymer, 44, 2003, 7529-7532). By carrying out the process of covalent cross-linking in a gel phase, the resultant graphenes can retain their structural integrity during the removal of the solvent. During subsequent steps, it is possible to minimise the effects of the meniscus associated with liquid-phase drying such that the mesopores within the gel structure can be prevented from collapsing, allowing for a cross-linked graphene network which is selected from an aerogel and a xerogel with high porosity and large surface area.

In the case where cross-linking is carried out by direct reaction between the oxides on the graphene surface, only a small proportion (approximately 1-3%) of the surface oxides react to form the cross-links between the graphenes. The cross-linked graphene network thus obtained will have unreacted oxide groups on the surface of the graphenes. These groups impart hydrophilicity (i.e. tendency to interact with or be dissolved by water and other polar substances) to the resulting graphene network which is selected from an aerogel and a xerogel.

However, in the case that a hydrophobic surface (one that repels water, and interacts with or dissolves in non-polar or neutral media) is required on the graphene, the method can further comprise a step of capping residual surface oxides on the graphene oxide prior to the removal of the solvent. Preferably, capping takes place after step (b) of the process and before step (c).

The term "capping" according to the present invention refers to any step which alters or transforms the surface oxides into other functionalities. In this respect, it can be any functional group which is able to react with the surface oxide group such as a metal, haloalkanes, acid halides and the like.

In a preferred embodiment, the surface oxides are capped using a hydrophobic functional group. In a particularly preferred embodiment, the hydrophobic functional group is preferably selected from the group consisting of haloalkyl, alkyl and siloxane, more preferably $C_{1-12}$ haloalkyl and $C_{1-18}$ alkyl, most preferably a $C_{1-12}$ haloalkyl and more preferably $C_{1-10}$ haloalkyl. Preferably the hydrophobic functional group is a haloalkyl containing more than 1 fluorine atom, preferably 3 to 20 fluorine atoms, preferably 8 to 16 fluorine atoms, more preferably 10 to 14 fluorine atoms, for example 13 fluorine atoms. Preferably the capping group reagent is a hydroxyhaloalkyl compound, preferably a $C_{1-12}$ hydroxyhaloalkyl compound, preferably trifluoroethanol. By hydrophobic, it is meant that the group imparts increased hydrophobic character to the graphene, thereby reducing the solid surface tension.

Where a linking molecule is used to form the cross-links, although only a small proportion of the carbon surface is involved with cross-linking, unlike the direct condensation reactions, the remaining surface will already be saturated with excess linking molecules. Since, both sides are saturated, these molecules are unlikely to covalently cross-link during drying (depending on the reagent), but may well be relatively polar and form undesirable non-covalent interactions that encourage collapse. In this case a further reaction with a capping agent, as described above, could be used to lower the surface tension, where the hydrophobic end group is reacted with the remaining unreacted end of the excess linking molecules.

In a further preferred method, the graphene gel is formed by using linking molecules that directly bond to the graphene surface, without using oxidised groups, using chemistries described above.

In another aspect of the present invention, a method may include the use of a blend of graphene or graphene oxide and a carbon nanotube network which is selected from an aerogel and xerogel, crosslinked by a mutually compatible chemistry as described for (oxidised) nanotubes.

In a further aspect of the present invention, a method may include the use of a blend of graphene and a carbon nanotube network which is selected from an aerogel and xerogel, crosslinked using linking molecules that directly bond to the graphene and nanotube surface using chemistries described above.

In the method according to the present invention, a solvent which is compatible with the graphene or graphene oxide is preferably used. In this respect, the term "compatible" refers to any solvent in which the graphene or graphene oxide forms a substantially homogeneous solution or dispersion. Preferably, the solvent which is compatible with the graphene or graphene oxide is miscible therewith. Preferably, the coupling agent is also substantially soluble in the solvent. In a preferred embodiment, the solvent is selected from dimethyl formamide, benzene, dichloromethane, chlorobenzene, chloroform, toluene, xylene, dioxane, dimethylsulfoxide, tetrahydrofuran, hexane, ethylene glycol, 1-propanol, ethanol, methanol, acetone, amide solvents and mixtures thereof, most preferably dimethyl formamide. As used herein amide solvents refers to any solvent which contains an amide group. Preferred amide solvents includes N-methyl-2-pyrrolidone and cyclohexyl pyrrolidone.

The graphene or graphene oxide may be present in the solvent at any given concentration. Preferably, the graphene or graphene oxide must be sufficiently concentrated that they can form a continuous connected network across the whole composition. Preferably, this concentration is above the rheological percolation threshold for the chosen graphene or graphene oxide dispersion in the chosen solvent. In a preferred method, the graphene or graphene oxide is present in the solvent at a concentration of between 0.01-30 vol. %, more preferably 0.1-20 vol. %, more preferably 1-5 vol. %.

In a further preferred method according to the present invention, the removal of solvent is carried out by solvent exchange with at least one solvent having lower surface tension than the initial solvent. The term "surface tension," as used herein, refers to the attractive force in any liquid exerted by the molecules below the surface upon those at the surface/air interface, which force tends to restrain a liquid from flowing. Preferably, the term "low surface tension," as used herein refers to liquids having a surface tension of less than or equal to about 30 mN/m as measured at 25° C. and atmospheric pressure. However, this value may be more or less, since the critical tolerable surface tension to avoid collapse during the drying step will depend on the network. In particular, as any one of the graphene thickness, the cross-link density, or degree of hydrophobisation increases, the need for low surface tension decreases. Therefore in principle, some graphene or graphene oxide gels may be dried without solvent exchange and others will need very low surface tensions. Whether a particular network requires such solvent exchange will depend on the individual properties of the gels. The lower density, higher surface area networks have more desirable properties but tend to be less robust so need solvent exchange or other controlled drying technique. In a particularly preferred embodiment, solvent exchange is carried out using acetone, followed by $C_3$-$C_{10}$ hydrocarbon, preferably hexane.

In a further aspect of the present invention, the aerogel or xerogel, may be synthesised in the presence of a one or more gelling agents to provide greater support to the gel-forming process. These agents may include polymers. A preferred polymer according to the present invention is carboxymethyl cellulose (CMC).

In one particularly preferred embodiment, the aerogel or xerogel may be synthesised by providing graphene and CMC or other polymer in water or other solvent, and freeze drying. In a further aspect of the present invention the aerogel or xerogel may be synthesised by providing oxidised graphene and CMC or other polymer in water or the solvent, and freeze drying.

In yet another aspect of the present invention the aerogel or xerogel may be synthesised by providing oxidised cross-linked graphene and CMC in water, and freeze drying.

In a further aspect of the present invention the aerogel or xerogel of the invention may be synthesised by providing graphene and CMC or other polymer in water or other solvent carrying out solvent exchange (preferably using water-acetone-hexane) and drying at ambient temperature and pressure.

In a further aspect of the present invention the aerogel or xerogel of the invention may be synthesised by providing oxidised graphene and CMC or other polymer in water or other solvent carrying out solvent exchange (preferably using water-acetone-hexane) and drying at ambient temperature and pressure.

In a further aspect of the present invention the aerogel or xerogel of the invention may be synthesised by providing oxidised cross-linked graphene and CMC or other polymer in water or other solvent carrying out solvent exchange (preferably using water-acetone-hexane) and drying at ambient temperature and pressure.

In a further aspect of the present invention the aerogel or xerogel of the invention may be synthesised by providing oxidised cross-linked graphene in water, and freeze drying. In a further aspect of the present invention the aerogel or xerogel may be synthesised by providing oxidised cross-linked graphene in water, carrying out solvent exchange (preferably using water-acetone-hexane) and drying at ambient temperature and pressure.

The graphene or graphene oxide network produced according to the present invention is preferably an aerogel or a xerogel, most preferably an aerogel.

As used herein, the term "aerogel" refers to a highly porous material of low density, which is prepared by forming a gel and then removing liquid from the gel while substantially retaining the gel structure. Preferably, an "aerogel" according to the present invention comprises a graphene or graphene oxide network wherein the volume change on drying of the gel is less than 30%, preferably less than 20%, preferably less than 10%, preferably less than 5%. Aerogels have open-celled microporous or mesoporous structures. Typically, they have pore sizes of less than 1000 nm and surface areas of greater than 100 $m^2$ per gram. Preferably they have pore sizes of less than 200 nm and surface areas of greater than 400 $m^2$ per gram. They often have low densities, e.g. from 500 $mg/cm^3$ down to as little as 1 $mg/cm^3$, preferably in the range of 15 to 300 $mg/cm^3$. Exceptionally, unlike other existing aerogels, those produced from graphenes or graphene oxide, may have low densities, high surface areas, but large pore sizes; in principle, the pore size may approach the scale of the individual graphene or graphene oxide lengths which can reach millimeters or even centimeters.

Preferably, aerogels are materials in which the liquid has been removed from the gel under supercritical conditions. In one method according to the present invention, removal of solvent may carried out by supercritical drying or lyophilisation to form an aerogel. The most common method for supercritical drying involves the removal of the solvent with supercritical carbon dioxide, and this may be used in the present invention.

In a preferred method according to the present invention, the drying process is preferably carried out at room temperature and/or ambient pressure. This method is a more versatile procedure to fabricate an aerogel since it does not require supercritical $CO_2$, or a freezing-vacuum process. The aerogel can be obtained by simply drying the gel. The objective is to evaporate the solvent producing the minimum volume reduction when obtaining the aerogel from the gel. The cross-linking between the graphenes and graphene oxides and the optional hydrophobic functionalisation of the graphene or graphene oxide surface assists this process. Moreover, we propose a solvent exchange process to a solvent with lower surface tension. The functionalisation during the preparation of the gel permits us to simplify the later drying step.

The term "xerogel" as used herein refers to a type of aerogel in which the volume change on drying of the gel is greater than approximately 30%. In this case, although the gel partially collapses during drying, the strong covalent network of graphenes or graphene oxides limits the process, yielding a more useful, more porous, less dense structure, than obtained from drying physical gels or other graphene or graphene oxide suspensions.

The pores in the aerogels of the present invention are typically filled with air. They can also be filled with other desired gases. Alternatively, the gases can be removed from the aerogel under vacuum.

Aerogels prepared according to the present invention allow the gel to be cast in predetermined shapes, for example as particles, to match the desired final aerogel particle size and shape. The idea is to control the final shape by controlling the shape in the gel phase. The present method also allows for the formation of a large gel to form a large aerogel. In this way, the large aerogel can be broken or otherwise processed into particles of the desired size. The aerogel may also be formed into particles such as beads or pellets (typical diameters in the mm range) which may be used as a catalyst support, or as films/sheets for use as filters.

It is desirable that the resultant graphene or graphene oxide network contains as few impurities as possible. Such impurities include residual reagents (e.g coupling agents), surfactants, additives, polymer binders and the like. This term however does not encompass any modification groups such as fluoroalkyl species that have subsequently been deliberately added to the graphene network, and preferably covalently bound to the network. The presence of these impurities can lead to an increase in the density of the networks as well as reducing the electrical conductivity and surface area of the aerogel. In the current invention, excess or exhausted small molecule coupling agents are easily removed during the solvent exchange process.

Since the method according to the present invention does not require the use of a substantial amount of such additives or reagents which are often hard to remove, graphene and graphene oxide networks which are selected from aerogels and xerogels with high electrical conductivity, large surface area and low density can be obtained.

In a preferred embodiment, the total amount of impurities present in the aerogel or xerogel produced by the present invention is less than 5 wt. %, and even more preferably less than 1 wt. %. This condition is particularly so at the point that the solvent has been removed, and prior to any subsequent modification of the network (aerogel or xerogel) required to produce a final material having a specific utility.

Preferably, each graphene and graphene oxide used in the present invention has high electric conductivity and allows a current flow at a current density of greater than 10 $MA/cm^2$, preferably greater than 100 $MA/cm^2$ or more. A network of graphenes and graphene oxides is therefore thought to display excellent electrical conductivity and current density, compared to existing carbon aerogels.

In addition, graphenes and graphene oxides have desirable intrinsic mechanical characteristics, including high strength, stiffness, and flexibility, at low density. These properties make graphenes and graphene oxides desirable for many industrial applications, and lend desirable properties to the resulting aerogel networks.

The shape of the aerogel or xerogel can be controlled by controlling the shape of the vessel used during the gelation step. The density of the final aerogel can be controlled by varying the volume fraction of graphene or graphene oxide within the initial gel.

In preferred embodiments, there are provided catalysts, catalyst supports, non-reflective panels, absorbents, filter materials, gas adsorption media, water purification media, substrates for cell growth and differentiation and electrochemical device electrodes comprising a graphene network which is selected from an aerogel and a xerogel prepared using the present method.

Heating Graphene or Graphene Oxide Aerogel/Xerogel

According to a further aspect of the present invention, there is provided a method of heating a graphene or graphene oxide aerogel or xerogel comprising the steps of: a) providing a graphene aerogel or xerogel; and, b) applying an electrical current thereto.

Any current may be applied to affect the heating. In a preferred embodiment, a current of up to 1 A, preferably between 3 and 500 mA, more preferably between 5 and 100 mA, more preferably between 6 and 18 mA is applied.

Any voltage may be applied to affect the heating. In a preferred embodiment, voltage of up to 240 V, preferably between 0.5 and 150 V, more preferably between 5 and 100 V, more preferably between 10 and 30 V is applied.

In a preferred embodiment, a current density of up to 500 $A/cm^2$, preferably between 0.1 $mA/cm^2$ and 100 $A/cm^2$, more preferably between 1 $mA/cm^2$ and 100 $mA/cm^2$, more preferably between 5 $mA/cm^2$ and 20 $mA/cm^2$ is achieved.

In a further preferred embodiment, electric fields of up to 100 V/cm, preferably between 0.001 and 20 V/cm, more preferably between 0.005 and 10 V/cm, more preferably between 0.1 and 1 V/cm is achieved.

The relationship between current, current density, voltage and electric field may be explained using the following equations.

$$I=V/R;\ R=\rho L/A;\ \sigma=1/\rho;\ J=\sigma E;\ \text{and,}\ E=-V/d$$

wherein
I=Current/A; V=Voltage/V; J=Current density/A/cm2; R=Resistance/Ohms; ρ=Resistivity/Ohm; σ=Electrical conductivity/S/m; E=Electric field/V/m; d=distance separating the electrodes/m; L=length/m; A=cross-sectional area perpendicular to current flow/m.

Preferably, the distance separating the electrodes is between 0.1 cm and 50 cm, preferably between 1 cm and 20 cm, more preferably between 2 cm and 10 cm.

Preferably, the electrode surface area of the electrodes is between 0.5 $cm^2$ and 100 $cm^2$, preferably between 1 $cm^2$ and 50 $cm^2$, more preferably between 2 $cm^2$ and 10 $cm^2$. Electrodes may be sheets, films, rods, wires, coatings, or other morphology of metallic conductor suitable for the application and aerogel geometry required. During fabrication, the aerogel may be gelled around or against the electrodes (which may be porous to assist mechanical interlocking). Alternatively, the electrodes may be pressed against or inserted into the aerogel after fabrication. Inert electrode materials, such as noble metals or conductive carbons, are preferred.

The electric field may then be calculated using the equation below:

$$E=-V/d$$

The power required to produce a specific heating effect may be calibrated as follows. The voltage may be measured using a conventional power supply and a conventional ammeter may be used to measure the current at each temperature.

According to the present invention, the aerogels and xerogels produced according to the present invention may be heated in an inert atmosphere to a temperature of up to 3273 K, preferably between 373 K and 1273 K, more preferably between 473 K and 773 K. If the aerogels or xerogels are heated in air, they may be heated to a temperature of up to 873 K, preferably between 373 K and 823 K, more preferably between 423 K and 773 K, even more preferably between 473 K and 723 K.

Heating the graphene aerogels or xerogels above approximately 773 K in inert atmosphere (preferably by electrical heating) would carbonise any polymer structure, forming a more stable carbonaceous binding of the junctions. Above approximately 2073 K, the graphene may graphitise and fuse together to form an inherently continuous and robust structure with a high degree of graphiticity.

In a further aspect of the present invention, heating of the aerogels or xerogels may be carried out by cycling between two or more temperatures. Accordingly, in one aspect of the invention, cycling is carried out between 100° C. and 1000° C., more preferably between 200° C. and 600° C., even more preferably between 300° C. and 400° C.

Graphene or graphene oxide aerogels and xerogels provide high electrical and thermal conductivity, to generate a robust, high surface area network that can be electrically-heated. By processing a graphene or graphene oxide aerogel or xerogel into a desired shape, a continuously-connected homogeneous network is provided, through which current can flow. Due to Joule heating within the branches of the network, the local temperature is raised throughout, by internal heating. The need for thermal diffusion is minimised and any local variations in temperature is reduced by the high thermal conductivity of the graphene. Furthermore, graphene and graphene oxide is stable to high temperatures, (at least 500° C. even under oxidising conditions, and much higher temperatures in inert atmospheres). The temperature within the network can be rapidly adjusted by varying the current or applied voltage to immediately vary the local Joule heating effect. In addition, graphene or graphene oxide aerogels and xerogels have very low heat capacity, helping to reduce response time.

The temperature may be monitored by one or more external thermocouple(s) placed in the aerogel or xerogel, or embedded during fabrication, or by optical pyrometry.

In a further embodiment according to the present invention, the measured resistance of the aerogel or xerogel itself may be used as an indication of temperature.

The heatable aerogel or xerogel may be used in a flow-through geometry, in which gas or liquid passes through the pores in the structure, coming into contact with the graphene surface (or, optionally, additional material supported on the graphene) and therefore also being heated to the desired temperature.

In one embodiment, the graphene or graphene oxide aerogel or xerogel may be used as a heater; the very high surface area, well-defined temperature, and homogeneous porosity/flow makes it a particularly effective gas or liquid heater.

The resistance at each temperature may be calculated from the current and voltage values. The temperature can be measured using an optical pyrometer, an embedded thermocouple, or other methods known in the art. The result will be a calibration relation between aerogel or xerogel resistance and temperature; this dependence will vary with device geometry and aerogel or xerogel density. In operation, the resistance can then be used to determine the temperature, and hence provide appropriate feedback control. In this way, the requisite heating can be predetermined for a given aerogel or xerogel by adjusting the applied voltage/current accordingly.

The heated medium may further comprise molecules that undergo chemical transition at the temperature within the network, optionally catalysed by the graphene or graphene oxide surface itself, or supported catalysts. The pure graphene or graphene oxide surface and defects thereon can act as catalysts, or the surface can be functionalised with molecular catalysts, or other nanoparticulates, by methods known in the art.

In yet another embodiment, the graphene or graphene oxide surface (or modifications) can act as a sorbent/filter either to purify a gas/liquid stream, or to store (a fraction of) it. Subsequently, heating of the graphene or graphene oxide aerogel or xerogel will regenerate the sorbent by decomposition or desorption of the trapped species. The heatable graphene or graphene oxide aerogel and xerogel provides advantages such as rapid and homogeneous heating, fast cycling, rapid emission of stored species, and minimal thermal degradation. Furthermore, accurate temperature control allows fractionation of adsorbed species by type.

In yet another embodiment, the heatable graphene or graphene oxide aerogel or xerogel can be used as a means to modify the network itself, by locally stimulating a temperature-dependent synthetic reaction on the carbon surface. Some examples include solvent-free reactions for the chemical modification of graphene surfaces (functionalisation of graphene) by thermal reaction with a suitable vapour and the nucleation, precipitation, or polymerization of a material onto the graphene, or graphene oxide.

Such approaches represent an approach to creating modified electrically-heatable networks for specific applications, as a more controlled alternative to more conventional approaches, such as incipient wetness, precipitation, or electrochemical deposition. They provide a means to add functional components (such as (electro)catalysts, sorbents, electrode components, etc) as well as to strengthen the network and adjust its physical characteristics.

DETAILED DESCRIPTION OF THE INVENTION

General

The term "comprising" encompasses "including" as well as "consisting" e.g. a composition "comprising" X may consist exclusively of X or may include something additional e.g. X+Y.

The term "about" in relation to a numerical value x means, for example, x+10%.

The word "substantially" does not exclude "completely" e.g. a composition which is "substantially free" from Y may be completely free from Y. Where necessary, the word "substantially" may be omitted from the definition of the invention.

As used herein, the term "alkyl" refers to a straight or branched saturated monovalent hydrocarbon radical, having the number of carbon atoms as indicated. By way of non limiting example, suitable alkyl groups include propyl, butyl, pentyl, hexyl, heptyl, octyl, nonyl, decyl, and the like.

As used herein, the term "graphene monolayer" means a single sheet of graphene.

As used herein, the term "graphene" preferably means graphene composed of 10 or fewer atomic layers of graphene monolayers, preferably fewer than 5 layers, preferably one layer.

As used herein, the term "graphene oxide monolayer" means a single sheet of graphene with one or more oxide groups present on the surface of the graphene.

As used herein, the term "graphene oxide" preferably means graphite composed of 10 or fewer atomic layers of graphene monolayers, preferably fewer than 5 layers, preferably one layer, at least one of which contains one or more oxide groups present on the surface thereof.

The term "graphene oxide" as used herein refers to any graphene with one or more oxide groups present on the surface of the graphene. In the present invention, the "oxide groups" are selected from the group consisting of quinones, ketones, lactones, pyrones, carboxylic acids, carboxylates, hydroxides and hydroxyl groups, and groups derivable from these via oxidation, and mixtures of two or more thereof. In a particularly preferred embodiment, the surface oxides are carboxylic and/or hydroxide groups.

A graphene monolayer has a structure which is one-atom-thick planar sheet of $sp^2$-bonded carbon atoms.

According to the invention, typical graphene flake widths are preferably in the range of 50 nm-100 µm, preferably 100 nm to 10 µm.

EXAMPLES OF THE PRESENT INVENTION

The following examples of the present invention are merely exemplary and should not be viewed as limiting the scope of the invention.

Example 1

An Aerogel according to the invention is produced according to reaction scheme 1:

Reaction Scheme 1

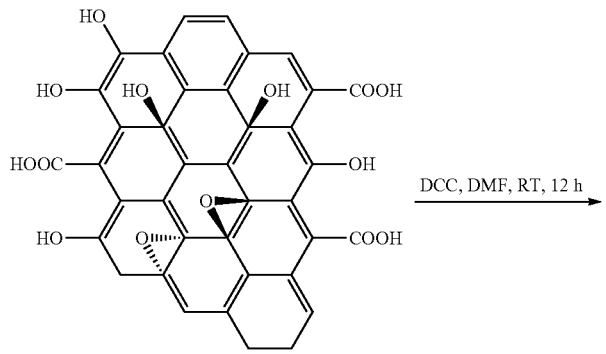

DCC, DMF, RT, 12 h

-continued

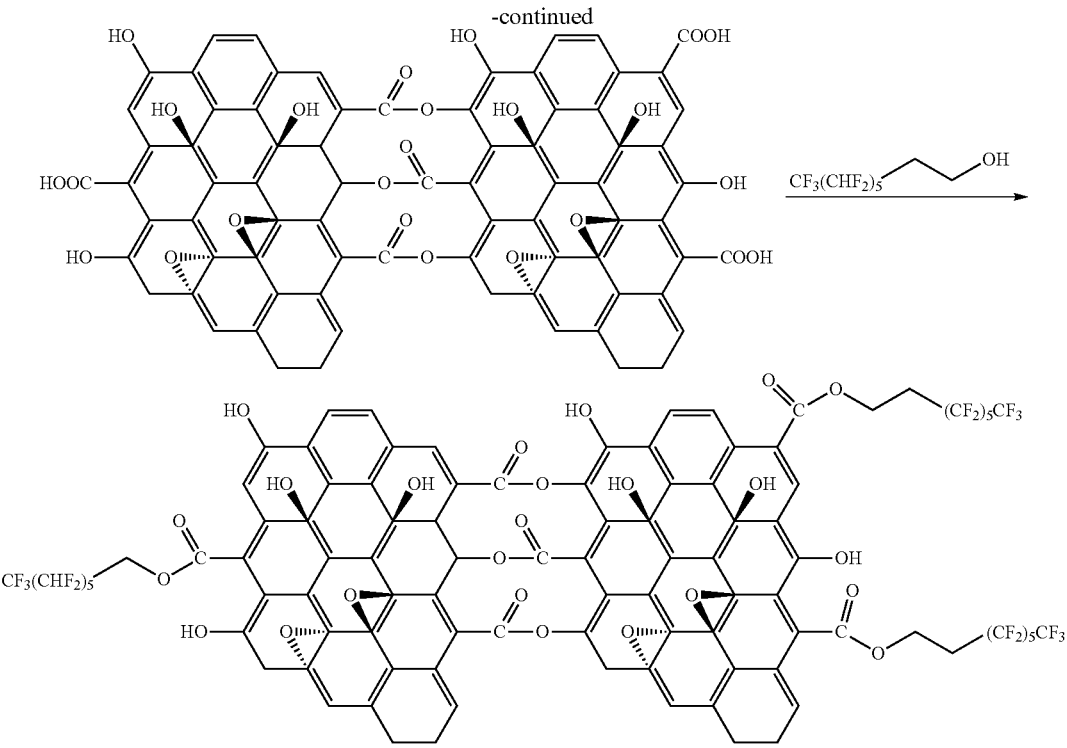

30

Crosslinking of the Graphene Oxide (Gelation)

400 mg of graphene oxide (Nanoinnova Technologies, L. T. D.) was placed under nitrogen in a rectangular 10 ml flask sealed with a septum. 1 mL of anhydrous dimethylformamide (99.8% Sigma-Aldrich) was injected using a syringe and the mixture was sonicated for 1 minute (ultrasonic bath Grant XUB5, 22.2 W/I) in order to obtain a homogeneous dimethylformamide graphene suspension. To this, 688 mg (10% carbon mol) of 1,3-dicyclohexylcarbodiimide (DCC, Fluka) was added to catalyse the esterification reaction between the alcohols and acid groups of graphene oxide. After 12 hours the black phase-presumably composed by crosslinked graphene-graphenes was highly viscous and did not deform even when the flask was turned upside down. The volume fraction of the graphene in the gel is estimated to be 15%.

Preparation of Hydrophobic Graphene Gel

In order to avoid the collapse of the gel during the drying of the solvent, the contact angle between the solvent and the graphenes was increased by introducing hydrophobic functional groups onto the graphene surface. This hydrophobisation was achieved through an additional esterification with a fluorinated alcohol; specifically, 0.8 ml (33% carbon mol) of 2,2,2-trifluoroethanol (ReagentPlus, 99%, Sigma-Aldrich) was added to the gel. After 12 hours the supernatant was set aside. In order to wash the sample, 2 ml of dimethylformamide were added to the gel and after 5 minutes the supernatant was set aside. The washing step was repeated up to 3 times.

Exchange the Pore Fluid with a Selected Solvent

The objective in this case is to exchange the pore fluid with the more hydrophobic n-hexane to reduce the effective surface tension during the drying of the gel. Since dimethylformamide and n-hexane are immiscible, acetone is used as an intermediate exchange agent as it is completely soluble in both liquids. Solvent exchange of pore-filled dimethylformamide with acetone and subsequently, of acetone with hexane was carried out. For this purpose 2 ml of the solvent were added to the gel and after 5 minutes the supernatant was set aside. The same process was repeated 3 times with each solvent. The sample was dried at room temperature to obtain the resulting graphene oxide aerogel.

Products

The shape of the aerogel can be modulated by controlling the shape of the vessel during the gelation step. The density of the final Aerogel can be modulated by varying the volume fraction of graphenes within the gel. For example, between at least the 15 vol % value described in the specific example and the percolation threshold of these specific crosslinked graphenes in dimethylformamide (estimated to be around 1 vol %).

The invention claimed is:

1. A method of producing an aerogel or xerogel comprising graphene, graphene oxide or a mixture thereof, comprising the steps of: a) dispersing graphene, graphene oxide or a mixture thereof in a solvent compatible therewith; b) cross-linking said graphene, graphene oxide or a mixture thereof by use of a coupling agent via functional groups present, on the graphene and/or the graphene oxide, or with a linking molecule comprising at least two functional sites capable of reacting with the surface of said graphene and/or graphene oxide, to form a covalently cross-linked gel network, wherein said coupling agent is selected from the group consisting of N,N'-dicyclohexylcarbodiimide (DCC), N,N'-diisopropylcarbodiimide (DIC), ethyl-(N',N'-dimethylamino)propylcarbodiimide hydrochloride (EDC), 4-(N,N-dimethylamino) pyridine (DMAP), (benzotriazol-1-yloxy)tris(dimethylamino)phosphonium hexafluorophosphate (BOP), (benzotriazol-1-yloxy)tripyrrolidinophosphonium hexafluorophosphate, bromotripyrrolidinophosphonium hexafluorophosphate, 0-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 0-(7-azabenzotriazol-1-yl)-N,N,N',N'-tetramethyluronium hexafluorophosphate (HATU), 0-(6-chlorobenzotriazol-1-yl)-N,N,N',N'-tetramethyluronium hexafluorophosphate (HCTU), 0-(3,4-Dihydro-4-oxo-1,2,3-benzotriazine-3-yl)-N,N,N',N' tetramethyluronium tetrafluoroborate (TDBTU), 3-(diethylphosphoryloxy)-1,2,3 benzotriazin-4(3H)-one (DEPBT) and carbonyldilmidazole (CDI), and mixtures thereof; and c) removing said solvent to produce a cross-linked aerogel or xerogel with a solvent content of less than 10%.

2. The method according to claim 1, wherein said cross-linking is carried out directly on the graphene pristine surface with a molecule selected from the group consisting of bis(diazonium) salts and multifunctional molecules suitable for 1,3-dipolar cycloadditions or Bingel condensations, or by the reduction of the graphenes followed by the reaction of the graphenes with an electrophilic cross-linking molecule.

3. The method according to claim 1, further comprising the step of capping residual functional groups on the graphenes prior to the removal of the solvent.

4. The method according to claim 1, wherein said solvent is selected from the group consisting of dimethyl formamide, benzene, dichloromethane, chlorobenzene, dichlorobenzene, chloroform, toluene, xylene, dioxane, dimethylsulfoxide, tetrahydrofuran, amide solvents and mixtures thereof.

5. The method according to claim 1, wherein said removal of solvent is carried out by solvent exchange with at least one solvent having lower surface tension than the solvent used in step (a).

6. The method according to claim 5, wherein said solvent exchange is carried out using acetone, followed by $C_3$-$C_{10}$ hydrocarbon, siloxane or fluorinated $C_3$-$C_{10}$ hydrocarbon.

7. A method of producing an aerogel or xerogel comprising graphene, graphene oxide or a mixture thereof, comprising the steps of: a) dispersing graphene, graphene oxide or a mixture thereof in a solvent compatible therewith; b) cross-linking said graphene, graphene oxide or a mixture thereof via functional groups present on the graphene and/or the graphene oxide, or with a linking molecule comprising at least two functional sites capable of reacting with the surface of said graphene and/or graphene oxide, to form a covalently cross-linked gel network, wherein said cross-linking is carried out directly on the graphene pristine surface with a molecule selected from the group consisting of bis(diazonium) salts and multifunctional molecules suitable for 1,3-dipolar cycloadditions or Bingel condensations, or by the reduction of the graphenes followed by the reaction of the graphenes with an electrophilic cross-linking molecule; and c) removing said solvent to produce a cross-linked aerogel or xerogel with a solvent content of less than 10%.

8. The method according to claim 7, wherein said cross-linking is achieved by using a coupling agent or by a dehydration step.

9. The method according claim 8, wherein said cross-linking is formed using a coupling agent which is selected from the group consisting of N,N'-dicyclohexylcarbodiimide (DCC), N,N'-diisopropylcarbodiimide (DIC), ethyl-(N', N'-dimethylamino)propylcarbodiimide hydrochloride (EDC), 4-(N,N-dimethylamino) pyridine (DMAP), (benzotriazol-1-yloxy)tris(dimethylamino)phosphonium hexafluorophosphate (BOP), (benzotriazol-1-yloxy)tripyrrolidinophosphonium hexafluorophosphate, bromotripyrrolidinophosphonium hexafluorophosphate, 0-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 0-(7-azabenzotriazol-1-yl)-N,N,N',N'-tetramethyluronium hexafluorophosphate (HATU), 0-(6-chlorobenzotriazol-1-yl)-N,N,N'N'-tetramethyluronium hexafluorophosphate (HCTU), 0-(3,4-Dihydro-4-oxo-1,2,3-benzotriazine-3-yl)-N,N,N',N' tetramethyluronium tetrafluoroborate (TDBTU), 3-(diethylphosphoryloxy)-1,2,3 benzotriazin-4(3H)-one (DEPBT) and carbonyldilmidazole (CDI), and mixtures thereof.

10. The method according to claim 7, further comprising the step of capping residual functional groups on the graphenes prior to the removal of the solvent.

11. The method according to claim 7, wherein said solvent is selected from the group consisting of dimethyl formamide, benzene, dichloromethane, chlorobenzene, dichlorobenzene, chloroform, toluene, xylene, dioxane, dimethylsulfoxide, tetrahydrofuran, amide solvents and mixtures thereof.

12. The method according to claim 7, wherein said removal of solvent is carried out by solvent exchange with at least one solvent having lower surface tension than the solvent used in step (a).

13. The method according to claim 12, wherein said solvent exchange is carried out using acetone, followed by $C_3$-$C_{10}$ hydrocarbon, siloxane or fluorinated $C_3$-$C_{10}$ hydrocarbon.

* * * * *